US00PP11922P2

(12) United States Plant Patent
Trees

(10) Patent No.: US PP11,922 P2
(45) Date of Patent: Jun. 12, 2001

(54) NEW GUINEA IMPATIENS PLANT NAMED 'BALCELILAE'

(75) Inventor: Scott C. Trees, Nipomo, CA (US)

(73) Assignee: Ball FloraPlant, a division of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 09/475,969

(22) Filed: Dec. 31, 1999

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Balcelilae', characterized by its light purple-colored flowers; upright and mounded plant habit; good basal branching and dark green leaves.

1 Drawing Sheet

BACKGROUND OF THE INVENTION

The present invention relates to a new and distinct cultivar of New Guinea Impatiens plant, botanically known as *Impatiens hawkeri,* and hereinafter referred to by the cultivar name Balcelilae.

The new Impatiens is a product of a planned breeding program conducted by the Inventor in Arroyo Grande, Calif. The objective of the breeding program was to develop new cultivars with freely-branching growth habit, numerous large flowers, and attractive flower and foliage colors.

The new Impatiens originated from a cross made by the Inventor of an unidentified selection of *Impatiens hawkeri* as the male, or pollen parent, with the *Impatiens hawkeri* cultivar Moorea, disclosed in U.S. Plant Pat. No. 9,147 as the female, or seed parent. The cultivar Balcelilae was discovered and selected by the Inventor as a flowering plant within the progeny of the stated cross in a controlled environment in Arroyo Grande, Calif. in 1997. Plants of the new Impatiens and the cultivar Moorea differ primarily in flower color.

Asexual reproduction of the new cultivar by terminal cuttings taken at Arroyo Grande, Calif., has shown that the unique features of this new Impatiens are stable and reproduced true to type in successive generations of asexual reproduction.

SUMMARY OF THE INVENTION

The following traits have been repeatedly observed and are determined to be the unique characteristics of 'Balcelilae'. These characteristics in combination distinguish 'Balcelilae' as a new and distinct cultivar:

1. Light purple-colored flowers with white centers.
2. Upright and mounded plant habit.
3. Good basal branching.
4. Dark green leaves.

The new Impatiens can be compared to the cultivar, Light Lavender II, disclosed in U.S. Plant Pat. No. 9,278. However, in side-by-side comparisons conducted by the Inventor in Arroyo Grande, Calif., plants of the new Impatiens differ from plants of the cultivar Light Lavender II in the following characteristics:

1. Plants of the new Impatiens have smaller leaves with shorter petioles than plants of the cultivar Light Lavender II.

2. Plants of the new Impatiens are not as freely flowering as plants of the cultivar Light Lavender II.

3. Flower color of plants of the new Impatiens is darker and more blue than flower color of plants of the cultivar Light Lavender II.

BRIEF DESCRIPTION OF THE PHOTOGRAPH

The accompanying photograph illustrates the overall appearance of the new cultivar as true as it is reasonably possible to obtain in colored reproduction of this type. Colors in the photographs may differ slightly from the color values cited in the detailed botanical description which more accurately describe the actual colors of the new Impatiens. The photograph comprises a top perspective view of a typical flowering plant of 'Balcelilae'.

DETAILED BOTANICAL DESCRIPTION

The cultivar Balcelilae has not been observed under all possible environmental conditions. The phenotype may vary somewhat with variations in environment such as temperature and light intensity, without, however, any variance in genotype. The following observations and measurements describe plants about 10 weeks after planting rooted cuttings and grown 10-cm pots in West Chicago, Ill., under commercial practice in a double-layered acrylic-covered greenhouse with day temperatures about 21° C., night temperatures about 19° C., and light levels about 2,500 to 3,500 footcandles.

In the following description, color references are made to The Royal Horticultural Society Colour Chart except where general terms of ordinary dictionary significance are used.

Botanical classification: *Impatiens hawkeri* cultivar Balcelilae.

Parentage:

*Male parent.*—Unidentified selection of *Impatiens hawkeri,* not patented.

*Female parent.*—*Impatiens hawkeri* cultivar Moorea, disclosed in U.S. Plant Pat. No. 9,147.

Propagation:

*Type cutting.*—Terminal cuttings.

*Time to initiate roots.*—About 7 days with 18° C.

*Time to develop roots.*—About 21 days with 18° C.

*Rooting description.*—Fibrous, fine, freely branching.

Plant description:

*Plant form.*—Upright and mounded.

*Growth and branching habit.*—Vigorous. Good basal branching, dense and bushy growth. Appropriate for 10 and 12.5-cm containers.

*Crop time.*—About 8 to 10 weeks are required to produce a finished flowering plant from a rooted cutting.

*Plant height.*—About 15.1 cm.

*Lateral branches.*—Diameter: About 7 mm. Internode length: About 4.5 cm. Color: Between 146B and 146C with 184B at the nodes and on older stems.

*Foliage description.*—Leaves simple, generally symmetrical, abundant, in whorls or opposite. Length: About 6.3 cm. Width: About 2.8 cm. Shape: Broadly lanceolate. Apex: Acute. Base: Attenuate. Margin: Serrulate with ciliation. Texture: Smooth, glabrous. Color: Young leaves, upper surface: 137A. Young leaves, lower surface: 137D. Fully expanded leaves, upper surface: Darker than 137A. Fully expanded leaves, lower surface: 137D. Venation, upper surface: 145B. Venation, lower surface: 145B. Petiole: Length: About 1 cm. Diameter: About 2 mm. Color: 145B.

Flower description:

*Flower type and habit.*—Light purple-colored flowers. Freely and continuously flowering. Flowers arise from leaf axils. Usually about eight flowers and flower buds per lateral branch. Flowers positioned mostly above the foliage and typically face upright and outward. Flowers roughly rounded in shape. Flowers persistent.

*Flowering season.*—Year-round under greenhouse conditions. In the garden, flowering is continuous from spring until fall.

*Flower buds.*—Length: About 2 cm. Diameter: About 1 cm. Shape: Ovoid. Color: Closest to 150D.

*Flower size.*—Diameter, about 6.3 cm; depth, about 1 cm.

*Petals.*—Quantity: Five, imbricate. Length: Upper petal, about 2.5 cm; lower petals, about 2 cm. Width: Upper petal, about 4.6 cm; lower petals, about 3 cm. Shape: Obovate to obcordate. Apex: Emarginate. Base: Attenuate. Margin: Entire. Texture: Smooth. Color: When opening, upper surface: 81C. When opening, lower surface: 75B. Fully opened, upper surface: Between 82B and 82C; base, 155D. Fully opened, lower surface: 82C; base, 155D.

*Spur.*—Length: About 5.5 cm. Shape: Narrow and curved. Color: 145D.

*Peduncles.*—Length: About 4.2 cm. Angle: Erect. Strength: Moderately strong. Color: Between 145B and 145C.

*Reproductive organs.*—Androecium: Stamen number: Five, anthers fused, filaments free. Anther shape: Obovate. Anther length: About 3 mm. Anther color: Transparent. Amount of pollen: Moderate. Pollen color: 158C. Gynoecium: Five-loculate fused. Pistil length: About 5 mm. Style color: 144A. Stigma color: 144C. Ovary color: 144A.

Disease resistance: Under commercial conditions, resistance to pathogens common to New Guinea Impatiens has not been observed.

Seed development: Seed production has not been observed.

It is claimed:

1. A new and distinct cultivar of New Guinea Impatiens plant named 'Balcelilae', as illustrated and described.

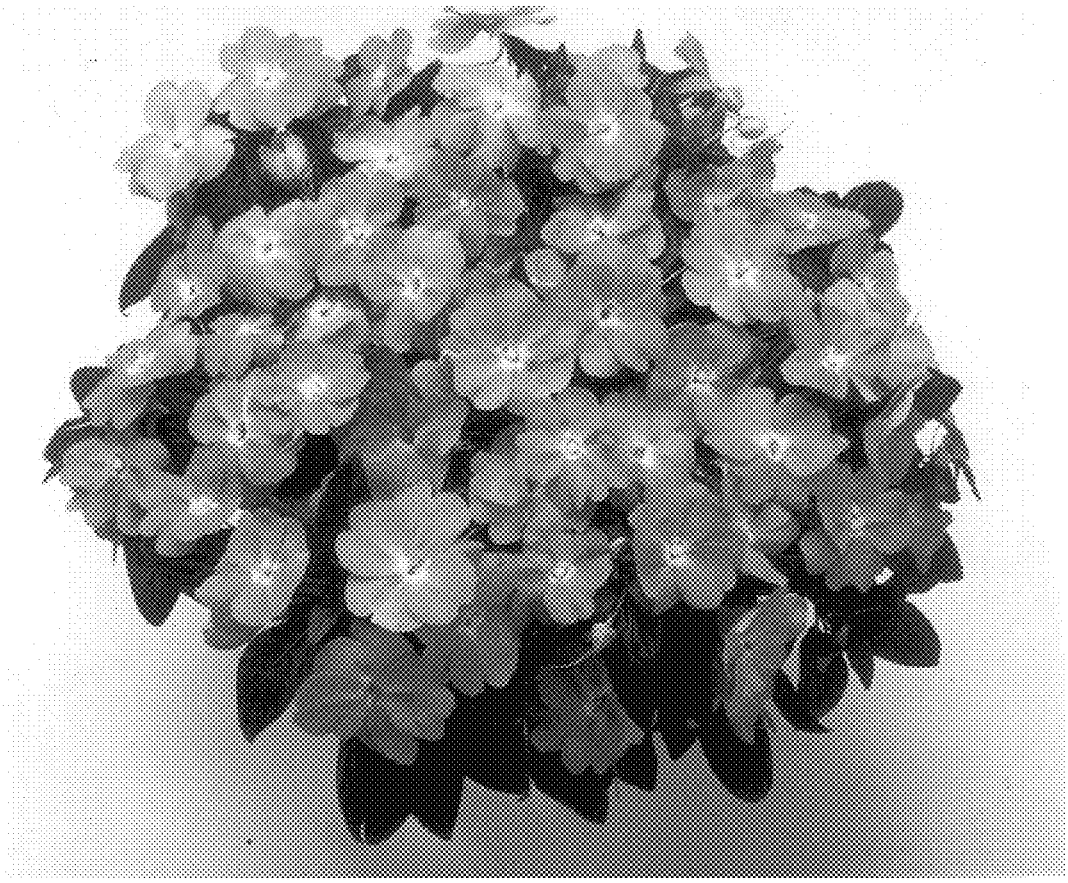

* * * * *